(12) United States Patent
Wurmbauer et al.

(10) Patent No.: US 10,183,128 B2
(45) Date of Patent: Jan. 22, 2019

(54) INJECTION DEVICE WITH NEEDLE SENSOR

(71) Applicant: Ares Trading SA, Aubonne (CH)

(72) Inventors: Werner Wurmbauer, Maria Saal (AT); Josef Schopf, Aichdorf/Fohnsdorf (AT); Bernhard Schatz, Klagenfurt (AT)

(73) Assignee: ARES TRADING SA, Aubonne (CH)

( * ) Notice: Subject to any disclaimer, the term of this patent is extended or adjusted under 35 U.S.C. 154(b) by 705 days.

(21) Appl. No.: 14/407,983

(22) PCT Filed: Jun. 11, 2013

(86) PCT No.: PCT/IB2013/001213
§ 371 (c)(1),
(2) Date: Dec. 15, 2014

(87) PCT Pub. No.: WO2013/186618
PCT Pub. Date: Dec. 19, 2013

(65) Prior Publication Data
US 2015/0182706 A1    Jul. 2, 2015

(30) Foreign Application Priority Data

Jun. 15, 2012 (EP) .................................... 12004541

(51) Int. Cl.
*A61M 5/50* (2006.01)
*A61M 5/34* (2006.01)
*A61M 5/24* (2006.01)
*A61M 5/31* (2006.01)

(52) U.S. Cl.
CPC ............ *A61M 5/5086* (2013.01); *A61M 5/24* (2013.01); *A61M 5/34* (2013.01); *A61M 2005/2407* (2013.01); *A61M 2005/3107* (2013.01); *A61M 2005/3118* (2013.01); *A61M 2205/14* (2013.01)

(58) Field of Classification Search
CPC ........ A61M 5/5086; A61M 5/24; A61M 5/34; A61M 2005/2407; A61M 2005/3107; A61M 2005/3118; A61M 2205/04
See application file for complete search history.

(56) References Cited

U.S. PATENT DOCUMENTS

| 3,630,417 | A | 12/1971 | De Haas | |
| 6,171,276 | B1* | 1/2001 | Lippe | ...................... A61M 5/20 |
| | | | | 128/DIG. 1 |
| 6,406,460 | B1 | 6/2002 | Hogan | |
| 7,704,231 | B2* | 4/2010 | Pongpairochana | ..... A61M 5/20 |
| | | | | 604/131 |
| 2008/0214916 | A1 | 9/2008 | Yodfat et al. | |
| 2011/0218384 | A1 | 9/2011 | Bachman et al. | |
| 2011/0288390 | A1 | 11/2011 | Yodfat et al. | |

(Continued)

FOREIGN PATENT DOCUMENTS

| WO | 0204049 A1 | 1/2002 |
| WO | 2005077441 A2 | 8/2005 |

(Continued)

*Primary Examiner* — Laura Bouchelle
(74) *Attorney, Agent, or Firm* — Kriegsman & Kriegsman

(57) ABSTRACT

An injection device for injecting liquid medicine to a patient comprises a medicine container (2) an end of which is connectable to a needle (3) and magnetic sensor means (21, 22) for sensing connection of the needle (3) to the medicine container (2).

9 Claims, 2 Drawing Sheets

(56) References Cited

U.S. PATENT DOCUMENTS

2015/0141923 A1 5/2015 Wurmbauer et al.
2015/0174324 A1 6/2015 Wurmbauer et al.

FOREIGN PATENT DOCUMENTS

WO 2008024814 A2 2/2008
WO 2013186617 A1 12/2013
WO 2013186619 A1 12/2013

* cited by examiner

Fig.3
Fig.4
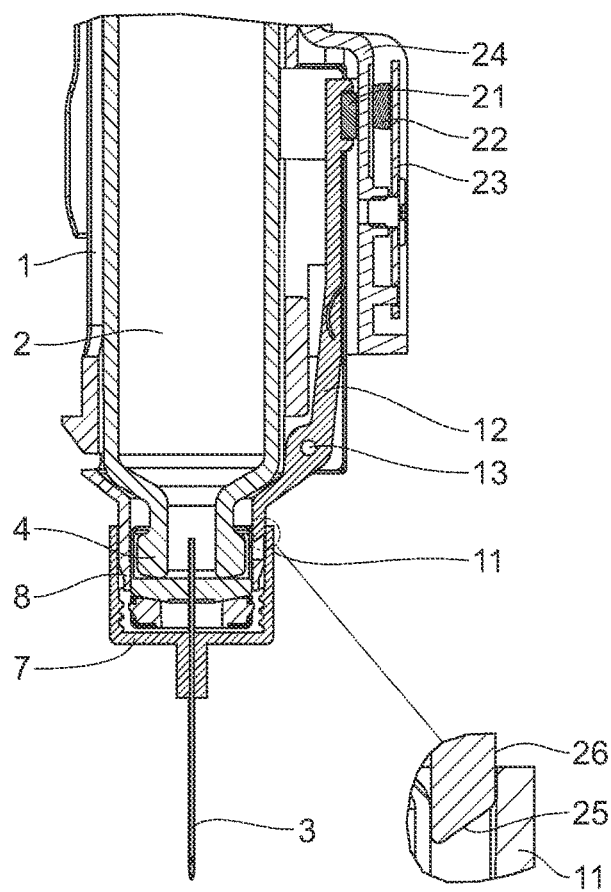
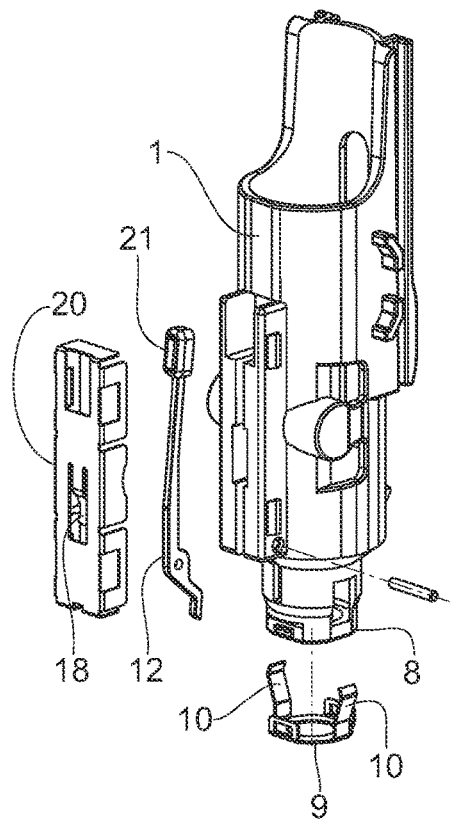

INJECTION DEVICE WITH NEEDLE SENSOR

The present invention relates to an injection device for injecting liquid medicine to a patient, of the type comprising a medicine container, such as a cartridge, connectable to a needle.

One such device is described in WO 2005/077441. In this device, optical sensor means are provided to sense whether a needle is connected to the cartridge. The optical sensor means comprise a light-emitting diode, a mirror and a photodiode. A light ray emitted by the light-emitting diode is reflected by the mirror toward the photodiode when no needle is properly connected to the cartridge. When a needle is properly connected to the cartridge, a support supporting the needle and fitted to the end of the cartridge pierced by the needle interrupts the light ray before it reaches the mirror so that the light ray is not received by the photodiode. Despite its being contact-free, such a sensor is sensitive to contamination by medicine. Liquid drops getting out from the needle may indeed contaminate the light-emitting diode, mirror and/or photodiode, and may thus disrupt the reception of the light ray by the photodiode while no needle is connected to the cartridge, causing a false needle detection to occur.

Another prior art document, U.S. Pat. No. 6,406,460, describes a syringe comprising a contact for detecting an electrical connection or a pressure when a needle is properly connected. Due to its being a contact and to its being positioned near the needle, such a sensor is still more sensitive to contamination by medicine than the sensor described in WO 2005/077441.

The present invention aims at providing an injection device having a needle sensor that is more resistant to contamination.

To this end, there is proposed an injection device for injecting liquid medicine to a patient, comprising a medicine container an end of which is connectable to a needle and magnetic sensor means for sensing connection of the needle to the medicine container.

Typically, the magnetic sensor means comprise:
a movable member actuable by connecting the needle to the medicine container and comprising a magnetic element,
a sensor element sensitive to a magnetic field generated by the magnetic element.

In a particular embodiment, the movable member is a lever comprising first and second ends, said lever being actuable at said first end by a needle support upon connection of the needle to the medicine container, said second end comprising the magnetic element.

Preferably, said second end is farther from said end of the medicine container than is said first end, and a distance between a hinge point of the lever and the second end is larger than a distance between said hinge point and the first end.

The injection device may further comprise a spring acting on the lever for maintaining the lever in a rest position when the needle is not connected to the medicine container.

Advantageously, a wall is provided between the magnetic element and the sensor element to protect the sensor element from contamination by the medicine.

Typically, said wall is made of a non-magnetic material.
The magnetic element is preferably a permanent magnet.
The sensor element may be a Hall effect sensor.

Other features and advantages of the present invention will be clearly apparent upon reading the following detailed description made with reference to the appended drawings in which:

FIG. 3 is a section view of the same portion of the injection device according to the invention, equipped with a properly connected needle;

FIG. 4 is an exploded perspective view showing several parts of said portion of the injection device according to the invention.

Figure 1:
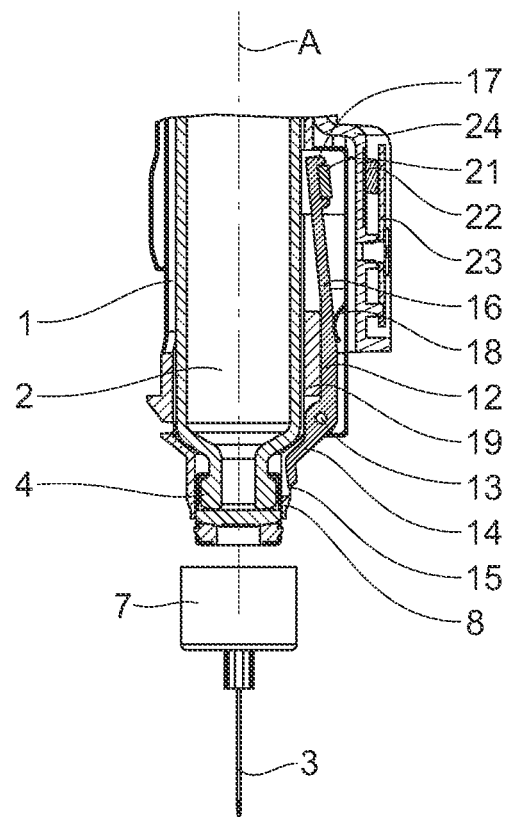
FIG. 1 is a section view of a portion of an injection device according to the invention, not equipped with a needle.

Referring to FIGS. 1 to 4, an injection device according to the invention comprises a holder 1 for receiving and holding a removable medicine cartridge 2. The injection device is of the type as described in WO 2005/077441. It thus includes, inside a housing (not shown), the cartridge holder 1, first electromechanical means for axially moving a piston of the cartridge 2 and second electromechanical means for axially moving a structure including the first electromechanical means and the cartridge holder 1.

A needle 3 may be connected to the lower end 4 of the cartridge 2. The needle 3 has a rear end 5 and a front end 6 which are intended to pierce the lower end 4 of the cartridge 2 and the skin of a patient, respectively. The needle 3 is fixed to and projects from a needle support or hub 7 which may fit onto a lower end 8 of the cartridge holder 1 while the lower end 4 of the cartridge 2 is pierced by the rear end 5 of the needle 3. The fitting of the needle support 7 onto the lower end 8 of the cartridge holder 1 may be achieved by means of an intermediate part 9 (see FIG. 4) fixed around the lower end 8 of the cartridge holder 1 and having elastic flanges 10. The elastic flanges 10 are compressed by the internal surface of a cylindrical wall 11 of the needle support 7 upon engagement of said cylindrical wall 11 around the lower end 8 of the cartridge holder 1. As a variant, the cartridge holder 1 could be arranged so that the needle support 7 may fit onto the lower end 4 of the cartridge 2 instead of onto the cartridge holder 1.

Figure 2:
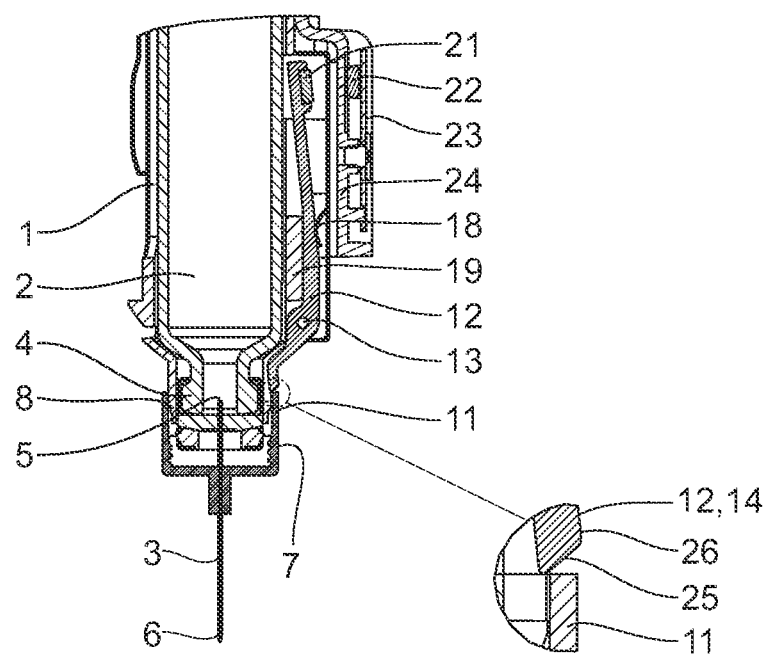
FIG. 2 is a section view of the same portion of the injection device according to the invention, equipped with an improperly connected needle.

A lever 12 is hinged at a hinge point 13 to the cartridge holder 1 and is generally oriented in the axial direction, represented by axis A, of the cartridge 2 and cartridge holder 1. The lever 12 defines a first arm 14 from the hinge point 13 to a lower end 15 of the lever 12 and a second arm 16 from the hinge point 13 to the upper end 17 of the lever 12. As can be seen, the second arm 16 is much longer than the first arm 14, more specifically the distance between the hinge point 13 and the upper end 17 is larger than the distance between the hinge point 13 and the lower end 15. In the absence of a needle at the lower end 4 of the cartridge 2, the lever 12 is held in a rest position by a spring 18 pressing the second arm 16 against a stop 19 (FIGS. 1 and 2). In the example shown, the spring 18 is a blade spring defined by a lever retaining part 20 fixed to the cartridge holder 1 (see FIG. 4). A magnet 21 is fixed at the upper end 17 of the lever 12 and faces a sensor 22 in a direction transverse to the axis A. The sensor 22 is typically a linear Hall effect sensor. The sensor 22 is mounted on a PCB (printed circuit board) 23 which is itself mounted on a fixed part of the injection device, i.e. a part that is fixed relative to the housing. The sensor 22 and the PCB 23 are protected from medicine drops accidentally getting out of the cartridge 2 by a wall 24 mounted on or defined by said fixed part. The wall 24 is made of a non-magnetic material such as plastic.

The wall 24 separates the sensor 22 and the PCB 23 from the portion of the injection device including the cartridge 2, the cartridge holder 1 and the lever 12 with its magnet 21.

Under the action of the second electromechanical means, the cartridge holder 1 and, with it, the cartridge 2 may move axially between a retracted, top position shown in FIGS. 1 to 3, in which the cartridge 2 and, if any, the needle 3 connected to it are located inside the housing, and a bottom position (not shown) in which the needle 3 protrudes axially outside the housing from an aperture thereof to pierce the patient's skin. The magnet 21 faces the sensor 22 when the cartridge holder 1 and the cartridge 2 are in the retracted position. Connection of the needle 3 to the cartridge 2 may be achieved by automatically moving the cartridge holder 1 down and then up after a needle cap accommodating the needle support 7 and the needle 3 fixed to it has been engaged into the said aperture of the housing by the user, as described in WO 2005/077441. As a variant, however, the present invention could apply to an injection device in which the cartridge is not movable and the needle may be connected only manually.

When no needle is connected to the cartridge 2 (see FIG. 1) or a needle 3 has been improperly or only partially connected (see FIG. 2), the lever 12 is in its rest position and the magnet 21 is at a certain distance from the sensor 22. Upon proper fitting of the needle support 7 onto the lower end 8 of the cartridge holder 1, the needle support 7 acts on the first arm 14 of the lever 12 to rotate the lever 12 against the force exerted by the spring 18 to an actuated position in which the magnet 21 is closer to the sensor 22 (see FIG. 3). To this end, the cylindrical wall 11 of the needle support 7 cooperates with a slanted surface 25 of the lower lever end 15. After the needle 3 and the needle support 7 have been fully assembled to the cartridge 2, the cylindrical wall 11 cooperates with a side surface 26 of the first lever arm 14 to hold the lever 12 in the actuated position.

Thus, in the actuated position of the lever 12 the sensor 22 receives a magnetic field of higher level than when the lever 12 is in the rest position. By comparing the level of magnetic field received with a predetermined threshold, the sensor 22 and its associated circuitry may determine when a needle has been properly connected. The control unit of the injection device may then decide to allow or not the injection.

Using magnetic sensor means as proposed by the present invention has been found to render the needle detection very resistant to contamination by medicine. Reliable detection may occur even when medicine leaked from the cartridge 2 or needle 3 has reached the area between the magnet 21 and the sensor 22. A magnetic sensor has also the advantage of not requiring a small distance between the movable member 12 (magnet 21) and the sensor 22 for the detection to occur. Thus, a sufficiently large distance may be provided between the magnet 21 in the actuated position of the lever 12 and the sensor 22 to enable provision of the protective wall 24.

Moreover, due to the great length of the second lever arm 16, the magnet 21 is located far from the lower end 4 of the cartridge 2 and, thus, the risk of the area between the magnet 21 and the sensor 22 being contaminated by medicine is not high.

Another advantage of the great length of the second lever arm 16, with respect to the first lever arm 14, is that a small displacement of the lower lever end 15 causes a large displacement of the upper lever end 17 and, therefore, of the magnet 21. Thus, the difference in the level of magnetic field received by the sensor 22 is higher and the reliability of the needle detection is increased.

The invention claimed is:

1. Injection device for injecting liquid medicine to a patient, comprising a medicine container an end of which is connectable to a needle, and further comprising a magnetic sensor means for sensing connection of the needle to the medicine container, wherein the magnetic sensor means comprises:
   a lever actuable by connecting the needle to the medicine container and comprising a magnetic element, the lever comprising first and second ends, and
   a sensor element sensitive to a magnetic field generated by the magnetic element.

2. Injection device according to claim 1, wherein the lever is actuable at said first end by a needle support upon connection of the needle to the medicine container, said second end comprising the magnetic element.

3. Injection device according to claim 2, wherein said second end is farther from said end of the medicine container than is said first end.

4. Injection device according to claim 3, wherein a distance between a hinge point of the lever and the second end is larger than a distance between said hinge point and the first end.

5. Injection device according to claim 2, further comprising a spring acting on the lever for maintaining the lever in a rest position when the needle is not connected to the medicine container.

6. Injection device according to claim 1, further comprising a wall between the magnetic element and the sensor element to protect the sensor element from contamination by the medicine.

7. Injection device according to claim 6, wherein said wall is made of a non-magnetic material.

8. Injection device according to claim 1, wherein the magnetic element is a permanent magnet.

9. Injection device according to claim 1, wherein the sensor element is a Hall effect sensor.

* * * * *